US00PP35339P2

(12) United States Plant Patent
van Swieten

(10) Patent No.: US PP35,339 P2
(45) Date of Patent: Aug. 22, 2023

(54) ***PHALAENOPSIS* ORCHID PLANT NAMED 'PHA602768'**

(50) Latin Name: ***Phalaenopsis* hybrid**
Varietal Denomination: PHA602768

(71) Applicant: ANTHURA B.V., Bleiswijk (NL)

(72) Inventor: Martinus Nicolaas Gerardus van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,998

(22) Filed: Feb. 24, 2023

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHA602768', particularly characterized by having white flowers with light purple edges and bright yellow and white lips, flowers that are concave in lateral view, lip curvature of lateral lobe is medium, and is propagated by meristem tissue culture, is disclosed.

3 Drawing Sheets

Genus and species: *Phalaenopsis* hybrid.
Variety denomination: 'PHA602768'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA602768'.

The new *Phalaenopsis* plant is a product of a planned breeding program conducted by the inventor in Bleiswijk, the Netherlands. The objective of this breeding program was to create a new *Phalaenopsis* plant with numerous attractive, white flowers with light purple edges, and bright yellow and white lips, suitable for potted plant production.

The new *Phalaenopsis* plant 'PHA602768' is a result of cross-pollination made by the inventor in May 2014 in Bleiswijk, the Netherlands, of the proprietary female, or seed parent, *Phalaenopsis* hybrid 'PHALGONDAL' (U.S. Plant Pat. No. 29,908) with the proprietary male, or pollen parent, *Phalaenopsis* hybrid '11-048283-0012' (unpatented).

The new *Phalaenopsis* was selected by the inventor as a single plant within the progeny of the stated cross-pollination in a controlled greenhouse in Bleiswijk, the Netherlands, in February 2017. Asexual reproduction of the new *Phalaenopsis* plant by meristem tissue culture since 2018 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 22, 2021 (Application no. 2021/1113), by Applicant who obtained the subject matter disclosed directly from the inventor. 'PHA602768' has not been made publicly available or sold anywhere in the world prior to the effective filing date of this application with the exception of sales or disclosures made one year or less before the effective filing date of this claimed invention by Applicant who obtained 'PHA602768' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA602768' as a new and distinct variety of *Phalaenopsis* plant:

1) White flowers with light purple edges and bright yellow and white lips;
2) Flower shape in lateral view is concave; and
3) Lip: curvature of lateral lobe is medium.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in October 2022. Colors in the photographs may differ from the color values cited in the detailed botanical description, which accurately describe the actual colors of the new variety.

DESCRIPTION OF THE NEW VARIETY

Figure 1:
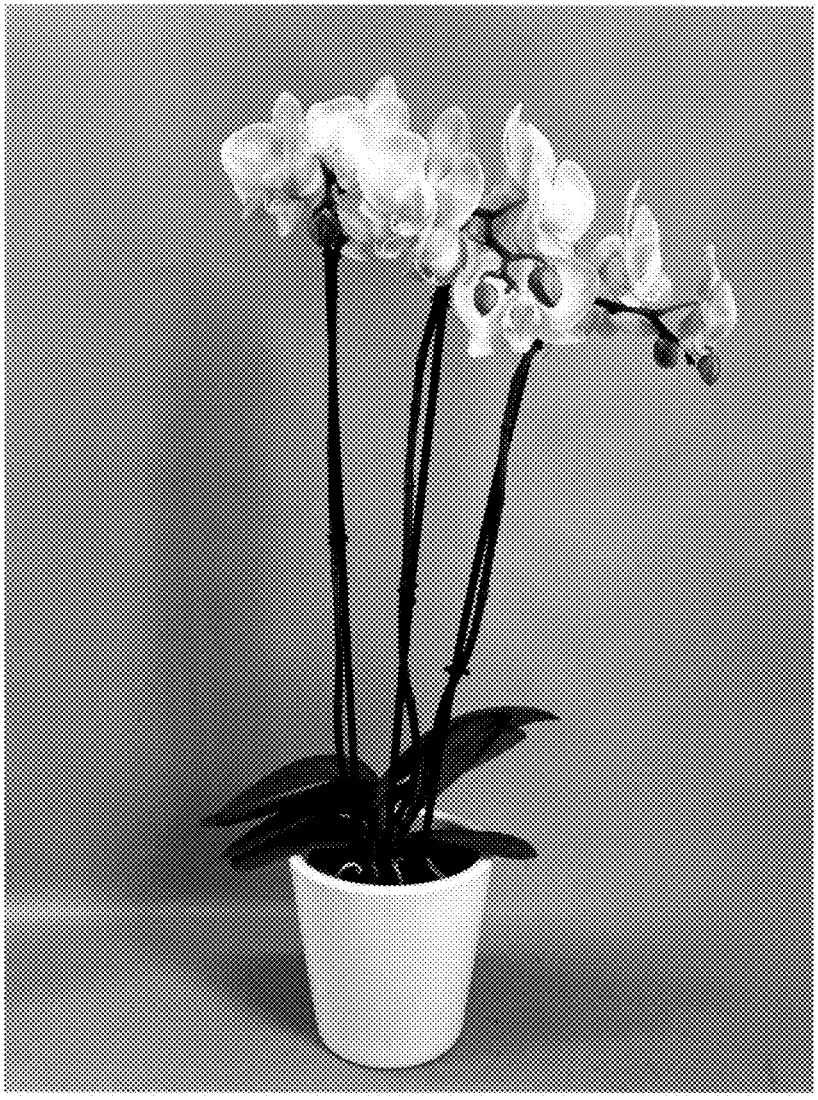
FIG. 1 shows the overall plant habit, including blooms, buds, and foliage of 'PHA602768'.
Figure 2:
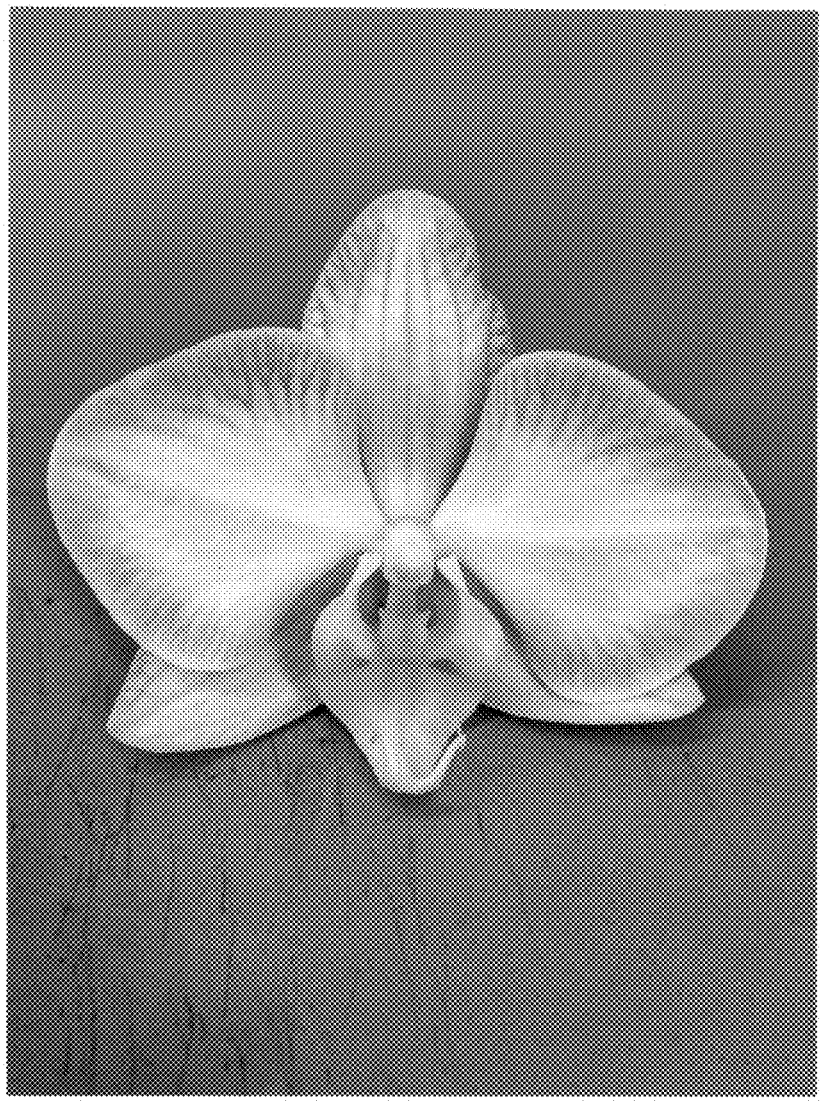
FIG. 2 shows a close-up of a flower of 'PHA602768'.
Figure 3:
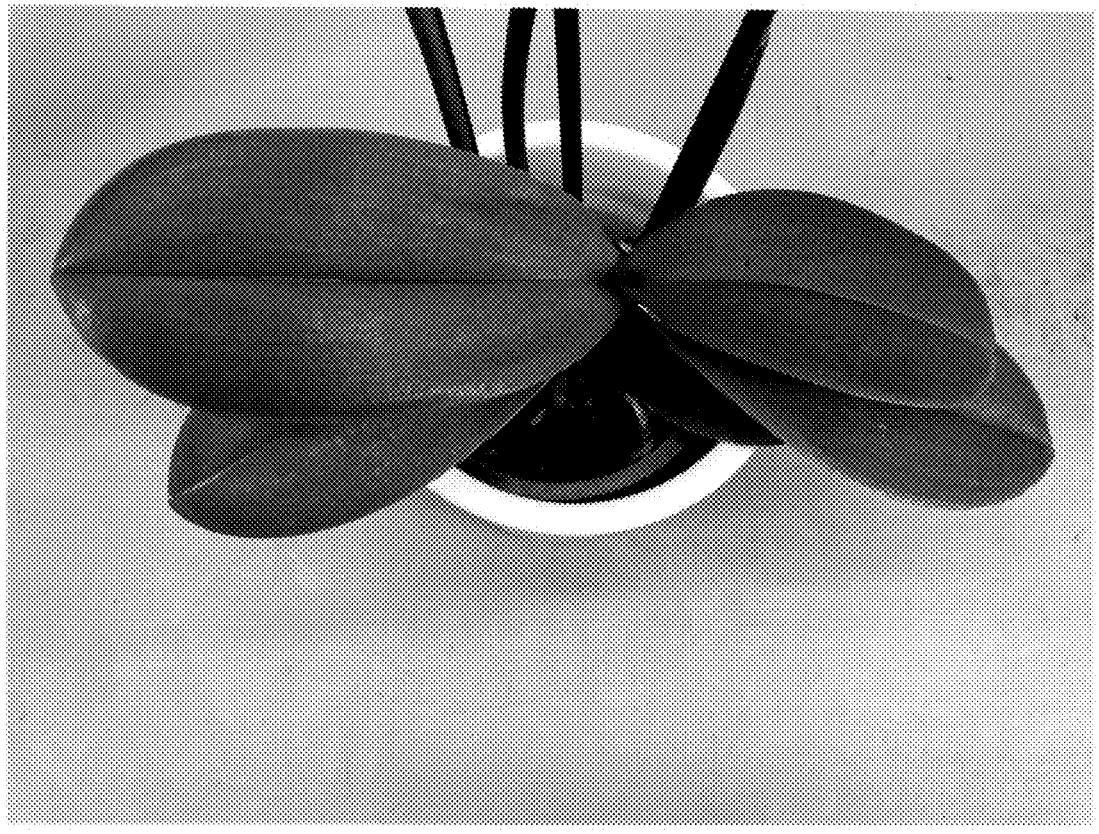
FIG. 3 shows an overhead view of the leaves of 'PHA602768'.

The following detailed description sets forth the distinctive characteristics of 'PHA602768'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in October 2022 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA602768'.

Parentage:

*Female parent*.—*Phalaenopsis* cultivar 'PHALGONDAL' (U.S. Plant Pat. No. 29,908).

*Male parent*.—*Phalaenopsis* cultivar '11-048283-0012' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS N144D) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height (from soil level to top of inflorescence)*.—Approximately 52.0 cm to 57.0 cm.

*Width (measured from leaf tips)*.—About 30.0 cm to 32.0 cm.

*Vigor*.—Strong.

Leaves:

*Mature leaves*.—Quantity per plant: 9 to 10 leaves are produced before flowering. Length (fully expanded): 13.0 cm to 15.0 cm. Width: 6.5 cm to 7.5 cm. Position of the broadest part of the leaf: At the middle. Shape: Oblong. Base shape: Moderately elongated. Apex: Obtuse asymmetric. Leaf blade angle with the petiole (measured from the horizontal position): Between 5 degrees and 25 degrees. Leaf margin: Entire. Color: Upper surface: Green (RHS 147A). Lower surface: Green (RHS 146A) with a dark red margin (RHS N186C). Texture (both upper and lower surfaces): Smooth. Thickness: 2.0 mm to 3.0 mm. Variegation: Absent. Venation: Pattern: Parallel. Color of the midvein: Upper surface: Green (RHS 147A). Lower surface: Yellow-green (RHS 146B).

Peduncle:

*Quantity per plant*.—1 to 3.

*Number of flowers per peduncle*.—7 to 9.

*Length*.—52.0 cm to 57.0 cm.

*Diameter*.—5.0 mm to 6.0 mm.

*Strength*.—Strong.

*Aspect*.—Upright to slightly pendent.

*Texture*.—Smooth.

*Color*.—Mix of yellow-green (RHS 146A) and reddish-brown (RHS 200B).

*Internode length*.—2.5 cm to 3.5 cm.

Inflorescence description:

*Appearance*.—Upright to slightly pendent, raceme inflorescence with bilaterally symmetrical flowers that open in succession beginning with the lowermost flower.

*Number of inflorescences*.—1 to 3.

*Inflorescence size*.—Height (from base to tip): 140.0 mm to 170.0 mm.

*Flowering time*.—First flowers can be expected 10 to 11 months after planting in a 12-cm pot.

*Flower*.—Height: 70.0 mm to 75.0 mm. Diameter: 90.0 mm to 95.0 mm. Depth of lip: 24.0 mm to 26.0 mm.

*Flower shape*.—Concave.

*Flower longevity*.—On the plant: 9 to 11 weeks.

*Fragrance*.—Absent.

*Flower bud*.—Average size: Large. Length: 28.0 mm to 30.0 mm. Width: 20.0 mm to 22.0 mm. Shape: Egg shaped. Color: Greenish-yellow (RHS 151D) with purplish-pink shade (RHS N78C).

*Petals*.—Arrangement: Open/free. Shape: Medium. Apex: Obtuse asymmetric. Margin: Weakly undulated. Length (from base to tip): 41.0 mm to 43.0 mm. Width: 44.0 mm to 46.0 mm. Position of the broadest part of the petal: Toward the base. Color (when fully opened): Upper surface: Basic color: White (RHS NN155C). Over color: Very light purple shade at the base and toward the edges (RHS 76B) and light purple stripes toward edges (RHS 76A). Lower surface: Basic color: White (RHS NN155C). Over color: Very light purple edges (RHS 76C). Number of spots and stripes on the petals (upper surface): Medium to many stripes RHS 76A. Color of spots and stripes on the petals (upper surface): RHS 76A. Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 44.0 mm to 46.0 mm. Width: 29.0 mm to 31.0 mm. Position of the broadest part of the dorsal sepals: At the base. Color (when fully opened): Upper surface: Basic color: White (RHS NN155C). Over color: Light purple shade (RHS 76A) and light reddish-purple stripes and netting (RHS N78D). Lower surface: Basic color: Light purple (RHS 76D). Over color: Light purple (RHS 76A) with a touch of light yellow-green (RHS 145D) at the base; diluting light reddish-purple stripes and netting (RHS N78D). Number of spots and stripes on the dorsal sepals (upper surface): Medium. Color of spots and stripes on the dorsal sepals (upper surface): RHS N78D.

Density of netting of the dorsal sepals (upper surface): Low. Color of the netting (upper surface): RHS N78D.

*Lateral sepals*.—Shape: Ovate. Apex: Obtuse asymmetric. Margin: Entire. Length (from base to tip): 45.0 mm to 47.0 mm. Width: 25.0 mm to 27.0 mm. Position of the broadest part of the lateral sepals: Toward the base. Color (when fully opened): Upper surface: Basic color: Very light purple (RHS 76C). Over color: Light yellow-green (a color in between RHS N144B and RHS 145C); light reddish-purple netting toward edges (RHS N78D). Lower surface: Basic color: Light purplish (RHS 76B) and light purple netting toward edges (RHS 76A). Over color: Light yellow-green (RHS 145C) and purplish-pink midvein (RHS N78C). Number of spots and stripes on the lateral sepals (upper surface): None. Color of spots and stripes on the lateral sepals (upper surface): Not applicable. Density of netting of the lateral sepals (upper surface): Very low. Color of the netting (upper surface): RHS 76A.

*Labellum* (*lip*).—Whiskers: Present. Length of whiskers: 19.0 mm to 21.0 mm. Color of whiskers: White (RHS NN155C) with light greenish-yellow tips (RHS 6B). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Moderately undulated. Length: 20.0 mm to 22.0 mm. Width: 15.0 mm to 17.0 mm. Color: Upper surface: White (RHS NN155C) with a touch of light greenish-yellow (RHS 4C) at the base toward one margin and greenish-yellow (RHS 6B) on the other side toward margin. Lower surface: White (RHS NN155C) with a touch of light greenish-yellow (RHS 4D) at the base toward one margin and greenish-yellow (RHS 6C) on the other side toward margin. Number of spots and stripes on the lateral lobe: None. Color of spots and stripes on the lateral lobe: Not applicable. Density of netting of the lateral lobe: None. Color of the netting: Not applicable.

*Apical lobe*.—Shape: Triangular. Margin: Entire. Length: 23.0 mm to 25.0 mm. Width: 25.0 mm to 27.0 mm. Color: Upper surface: Greenish-yellow (RHS 5A) at the base; white (RHS NN155C) toward whiskers. Lower surface: Greenish-yellow (RHS 5B) at the base; white (RHS NN155C) toward whiskers. Number of spots and stripes on the apical lobe: None. Color of spots and stripes on the apical lobe: Not applicable. Density of netting of the apical lobe: None. Color of the netting: Not applicable. Bump and ridge: Absent.

*Callus*.—Average size: Medium. Height: 6.0 mm to 7.0 mm. Length: 6.0 mm to 7.0 mm. Width: 4.0 mm to 5.0 mm. Color: Greenish-yellow (RHS 6A); yellow (RHS 9A) toward tips; light greenish-yellow (RHS 4C) on sides.

Reproductive organs:

*Column*.—Length: 9.0 mm to 10.0 mm. Diameter: 5.0 mm to 6.0 mm. Color: White (RHS NN155C).

*Pollinia*.—Quantity: 2. Diameter: 1.0 mm to 1.2 mm. Color: Orange (RHS 24A).

*Ovary*.—Length: 10.0 mm to 12.0 mm. Diameter: 2.9 mm to 3.3 mm.

*Pedicel*.—Length: 37.0 mm to 39.0 mm. Diameter: 3.4 mm to 3.7 mm. Color: Yellow-green (RHS 146D) at the base; light yellow-green (RHS 145C) with a touch of very light purple (a color in between RHS 76B and RHS 76C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA602768' differs from the female parent plant 'PHALGONDAL' (U.S. Plant Pat. No. 29,908) in that 'PHA602768' has obtuse petal apexes, edged flower pattern, and white ground color of upper side of flowers, whereas 'PHALGONDAL' has emarginated petal apexes, shaded flower pattern, and light purple ground color of upper side of flowers.

The male parent plant of 'PHA602768', '11-048283-0012' (unpatented), is no longer in existence therefore a meaningful comparison cannot be made.

'PHA602768' is most similar to the commercial *Phalaenopsis* plants named 'PHALDALWOJ' (unpatented) and 'PHALIPUE' (U.S. Plant Pat. No. 33,312). 'PHA602768' differs from the commercial variety 'PHALDALWOJ' in that 'PHA602768' is a medium to long plant with medium whiskers that are white with greenish-yellow tips, whereas 'PHALDALWOJ' is a very small to small plant with short whiskers that are very light purple with reddish-purple margins and light yellow-green tips. 'PHA602768' differs from the commercial variety 'PHALIPUE' in that 'PHA602768' has petals that are very light purple, greenish-yellow callus, and medium whiskers that are white with greenish-yellow tips, whereas 'PHALIPUE' has petals that are reddish-purple, yellow callus, and medium to long whiskers that are light purple with greenish-yellow tips.

I claim:

1. A new and distinct variety of *Phalaenopsis* plant named 'PHA602768', substantially as described and illustrated herein.

* * * * *